(12) United States Patent
Anderson et al.

(10) Patent No.: US 8,753,363 B2
(45) Date of Patent: Jun. 17, 2014

(54) VESSEL OCCLUSIVE DEVICE AND METHOD OF OCCLUDING A VESSEL

(75) Inventors: David W. Anderson, Brooklyn Park, MN (US); Bernard J. Esarey, Maplewood, MN (US); Gerald W. Timm, Minneapolis, MN (US)

(73) Assignee: GT Urological, LLC, Minneapolis, MN (US)

( * ) Notice: Subject to any disclaimer, the term of this patent is extended or adjusted under 35 U.S.C. 154(b) by 109 days.

(21) Appl. No.: 13/352,787

(22) Filed: Jan. 18, 2012

(65) Prior Publication Data

US 2012/0184980 A1 Jul. 19, 2012

Related U.S. Application Data

(60) Provisional application No. 61/461,290, filed on Jan. 18, 2011.

(51) Int. Cl.
*A61B 17/122* (2006.01)

(52) U.S. Cl.
USPC ............... 606/157; 600/30; 600/37; 606/203

(58) Field of Classification Search
CPC ... A61B 17/1322; A61F 2/0036; A61F 5/005; A61F 5/0066
USPC ......... 606/157, 151, 201, 202; 600/29, 30, 37
See application file for complete search history.

(56) References Cited

U.S. PATENT DOCUMENTS

| | | |
|---|---|---|
| 3,863,622 A | 2/1975 | Buuck |
| 3,903,894 A | 9/1975 | Rosen et al. |
| 4,118,805 A | 10/1978 | Reimels |
| 4,222,377 A | 9/1980 | Burton |
| 4,412,530 A | 11/1983 | Burton |
| 4,878,889 A | 11/1989 | Polyak |
| 4,938,760 A | 7/1990 | Burton et al. |
| 4,994,020 A | 2/1991 | Polyak |
| 5,509,888 A | 4/1996 | Miller |
| 5,518,504 A | 5/1996 | Polyak |
| 5,562,598 A | 10/1996 | Whalen et al. |

(Continued)

OTHER PUBLICATIONS

International Search Report for international application No. PCT/US2012/021713, dated Jul. 2, 2012 (5 pages).

(Continued)

*Primary Examiner* — Melanie Tyson
*Assistant Examiner* — Katelyn Bernier
(74) *Attorney, Agent, or Firm* — Hamre, Schumann, Mueller & Larson, P.C.

(57) ABSTRACT

An implantable vessel occlusive device and method for occluding a vessel are described, for example to occlude the urethra or bladder neck. The devices and methods described utilize an occlusive member connected to a control mechanism. The occlusive member is reversibly changed from a non-occlusive condition to an occlusive condition, for example by depressing an activation button contained within a resilient, elastomeric cover surrounding the control mechanism. In the occlusive position, an initial tension is applied to the occlusive member through a tensioning suture. The tension is translated into an occlusive pressure applied to the urethra or bladder neck that is sufficient to prevent urinary leakage. The non-occlusive position can be obtained by depressing the de-activation button. The occlusive member is constructed to allow elution of drugs, such as may be required to combat infection or tissue encapsulation from its surface.

17 Claims, 12 Drawing Sheets

(56) References Cited

U.S. PATENT DOCUMENTS

| | | | |
|---|---|---|---|
| 5,704,893 | A | 1/1998 | Timm |
| 5,888,188 | A | 3/1999 | Srougi et al. |
| 6,045,496 | A | 4/2000 | Pacella et al. |
| 6,074,341 | A | 6/2000 | Anderson et al. |
| 6,117,067 | A | 9/2000 | Gil-Vernet |
| 6,463,935 | B1 | 10/2002 | Forsell |
| 6,540,665 | B1 | 4/2003 | Connolly |
| 6,709,385 | B2 | 3/2004 | Forsell |
| 7,060,080 | B2 | 6/2006 | Bachmann |
| 7,798,954 | B2 * | 9/2010 | Birk et al. ............ 600/37 |
| 8,007,429 | B2 | 8/2011 | Anderson et al. |
| 8,062,205 | B2 | 11/2011 | Timm et al. |
| 2002/0111530 | A1 | 8/2002 | Bakane |
| 2004/0162460 | A1 | 8/2004 | Shah et al. |
| 2004/0267292 | A1 * | 12/2004 | Byrum et al. ............ 606/157 |
| 2005/0143765 | A1 * | 6/2005 | Bachmann et al. ........ 606/157 |
| 2006/0264697 | A1 | 11/2006 | Timm et al. |
| 2007/0027356 | A1 * | 2/2007 | Ortiz ............ 600/37 |
| 2007/0167672 | A1 * | 7/2007 | Dlugos et al. ............ 600/37 |
| 2009/0012351 | A1 * | 1/2009 | Anderson et al. ............ 600/30 |
| 2009/0062825 | A1 * | 3/2009 | Pool et al. ............ 606/157 |
| 2009/0222031 | A1 * | 9/2009 | Axelsson ............ 606/157 |
| 2010/0228080 | A1 * | 9/2010 | Tavori et al. ............ 600/37 |

OTHER PUBLICATIONS

Written Opinion of the International Searching Authority for international application No. PCT/US2012/021713, dated Jul. 2, 2012 (5 pages).

* cited by examiner

VESSEL OCCLUSIVE DEVICE AND METHOD OF OCCLUDING A VESSEL

CROSS-REFERENCE TO RELATED APPLICATIONS

The present application claims the benefit of U.S. Provisional Patent Application Ser. No. 61/461,290 entitled "TAPE MECHANICAL OCCLUSIVE DEVICE" filed on Jan. 18, 2011, which is herewith incorporated by reference in its entirety.

This invention was made with government support under SBIR Grant Number 1 R43 DK076397 01A1 awarded by the National Institutes of Health. The government has certain rights in the invention.

FIELD

This document generally relates to an occlusive device for occluding fluid conveying vessels in the body and particularly, but not by way of limitation, to a urethral occlusive device for preventing urinary incontinence.

BACKGROUND

Vessel occlusive devices are well known and commonly referred to as "artificial sphincters." They are installed within the body to aid or replace the natural sphincter of the body. For example, men can become urinary incontinent for example following surgeries to remove cancerous prostates. Women can become incontinent for example due to the pelvic trauma caused during childbirth and due to a laxity of the pelvic muscles occurring due to aging. Further, men and women may be rendered incontinent due to for example trauma, infection and/or birth defects.

Urethral occlusive devices can be used to restore urinary continence to patients with urinary control problems caused by various neurological diseases, surgical procedures, spinal cord injury, etc. Other occlusive devices include those used for contracting the bowel to prevent fecal leakage, for contracting the esophagus to prevent gastro-esophageal reflux, or those used in the area of gastric banding for restricting the stomach in treatment for obesity, and occlusion of the seminal vesicles or fallopian tube to control male and/or female fertility, of which there are needs that exist for commercial devices that can be used in such applications.

In particular, devices utilizing hydraulic sphincters or cuffs described in U.S. Pat. Nos. 3,863,622; 4,222,377, 4,412,530 and 4,878,889, have been used to provide urethral occlusion. To use these types of devices, the patient squeezes a control pump, which transfers fluid from a cuff to a pressure regulating balloon. The balloon forces the fluid through a fluid restrictor and back into the cuff to reestablish an occlusive urethral pressure within 3-5 minutes. These urethral occlusive devices are complicated to implant. One problem with hydraulic sphincters or cuffs is that they often do not apply uniform pressure on the urethra. As the cuff or sphincter is inflated, it folds or changes its shape, often in a non-uniform manner, thereby exerting uneven occlusive force on the urethra. This can result in urinary leakage, urethral erosion, or the urethra tissue being worn away after extensive use.

In other examples, the American Medical Systems, Inc. AUS 800 is a totally implantable hydraulic sphincter implanted in both males and females experiencing urinary incontinence and has been on the market for more than 35 years. The AUS 800 and its predecessors are described in U.S. Pat. Nos. 3,863,622, 4,222,377, 4,412,530 and 4,878,889.

The AUS 800 may have a silicone pressure regulating balloon implanted in the prevesical space, a silicone control pump implanted in the scrotum or labia and a silicone urethral occlusive cuff wrapped around the bulbous urethra in males or bladder neck in females. Each component may be filled with saline or radiopaque contrast media, and tubing emanating from each component may be routed between incisions for appropriate connections. The device can be deactivated for a period of approximately 6 weeks to allow tissue healing to proceed and urethral edema to subside. At activation, the control pump may be squeezed sharply to unseat a poppet and open operational fluid flow paths. The patient is taught to operate the device by squeezing the control pump through the scrotal or labial skin. This action can transfer fluid from the cuff to the pressure regulating balloon. The balloon can force the fluid through a fluid restrictor and back into cuff to reestablish an occlusive urethral pressure within 3-5 minutes. The AUS 800 can be complicated to implant and prone to fluid leakage, and may cause urethral atrophy and erosion. The complexity of its implantation is partly due to the requirement to intra-operatively fill and assemble its three components. The AUS 800 often fails due to wear in its componentry which leads to fluid leakage and post-operative infections. Urethral atrophy and erosion sometimes occur and are suspected to be due to the crenate shape of its occlusive cuff. Post-operative infection requiring explanation of the device also is a frequent complication. Despite these drawbacks, the AUS 800 is the only commercially available artificial urinary sphincter currently. The AUS 800 is available with a number of occlusive pressure ranges with 61-70 cm $H_2O$ being the pressure most frequently selected.

U.S. Pat. Nos. 5,704,893 and 6,074,341 discuss other types of urethral occlusive devices, which are entirely implantable artificial urinary sphincters. These artificial urinary sphincters are one-piece devices that do not require saline filling or intra-operative assembly, but where depression of a deactivation plunger, for example through the scrotal skin, causes a urethral occlusive sheath to expand and remove occlusive pressure from the urethra to allow normal urination. Depression of an activation button allows the occlusive sheath to contract and reapply urethral pressure to prevent urethral leakage. While such devices provided significant improvement in vessel occlusion, implantation in humans was impeded by growth of tough, fibrous tissue around the device, due to the natural defenses of the human body, which over time prevented expansion of the occlusive sheath.

SUMMARY

Generally, vessel occlusive devices are described and methods for occluding a vessel or vessels that convey fluid in humans and animals are described. Vessel occlusive devices as described herein generally include an occlusive member and a control mechanism for actuating the occlusive member into occluding and non-occluding positions.

One embodiment of the vessel occlusive device may include an outer sheath. One embodiment of the outer sheath may be a resilient tubular structure. The outer sheath may have a space inside the outer sheath, and the outer sheath is configured to retain liquid inside the space. At least a portion of the outer sheath is configured to encircle a fluid conveying body vessel. An inner occlusive tape is disposed through the space of the outer sheath. One end of the occlusive tape is fixed to an end of the outer sheath, and the other end of the inner occlusive tape is freely movable relative to the outer sheath. A control mechanism is connected to the free end of the inner occlusive tape. When the control mechanism applies a tension to the inner occlusive tape, the inner occlusive tape applies a pressure to the portion of the outer sheath encircling the fluid conveying body vessel; and when the control mechanism releases the tension from the inner occlusive tape, the inner occlusive tape releases the pressure to the portion of the outer sheath encircling the fluid conveying body vessel.

Another embodiment of the vessel occlusive device may have an inner occlusive tape that has a varied width from the first end to the second end of the inner occlusive tape. One embodiment of the inner occlusive tape may have a varied width that is tapered. A preset portion of the varied width may encircle a circumference of a vessel when implanted.

In some embodiments of the vessel occlusive device, the size of the portion of the outer sheath that is configured to encircle a fluid conveying body vessel may be adjusted to accommodate the anatomically variable structures of the body vessel. In some embodiments, an outer surface of the outer sheath may have a sizing band. The sizing band may have a plurality of locking detents. The locking detents may engage to a locking clip of the occlusive device. By locking the outer sheath at different locking detents, the size of the portion of the outer sheath that encircles the body vessel may be adjusted.

In yet another embodiment of the vessel occlusive device, a bleed valve may be connected to one end of the outer sheath and in fluid communication with the space of the outer sheath. The bleed valve may have an open position and a closed position; and the open position is configured to allow air to escape out of the space of the outer sheath and the closed position is configured to be water tight.

A method of applying an occlusive pressure to a tubular body passage may include implanting an occlusive device inside a body. The occlusive device may have an occlusive member that has an outer sheath and an inner occlusive tape. The inner occlusive tape may be disposed through a space of the outer sheath. One end of the occlusive tape is fixed to an end of the outer sheath, and the other end of the inner occlusive tape is freely movable relative to the outer sheath. A portion of the outer sheath may be wrapped at least partially around a vessel. A liquid may be added to the space of the outer sheath and the outer sheath can retain the fluid in the space. A tensioning force may be applied to one end of the inner occlusive tape so that the inner occlusive tape applies a pressure to the portion of the outer sheath wrapping the tubular body passage.

The inner occlusive tape may have varied width along its length. A method of applying an occlusive pressure to a tubular body passage may also include the step of positioning a predetermined portion of the varied width of the inner occlusive tape so that the predetermined portion of the varied width encircle a circumference of a vessel.

BRIEF DESCRIPTION OF THE DRAWINGS

The drawings, which are not necessarily drawn to scale, illustrate generally, by way of example, but not by way of limitation, various embodiments discussed below.

FIG. 2A shows an inner surface of the occlusive member that is configured to be in contact with a vessel when in use. FIG. 2B shows an outer surface of the occlusive member that is configured to be away from the vessel when in use.

FIG. 6A shows an occlusive member of the occlusive device configured to fit a larger vessel than the vessel that the occlusive device in FIG. 6B is configured to fit.

FIG. 7A shows a clip prior to engagement of an occlusive member. FIG. 7B shows the clip following the engagement of the occlusive tape.

FIG. 10A shows the bleed valve in an open position, and FIG. 10B shows the bleed valve in a closed position.

FIG. 14A shows the sling occlusive member in non-occluding position, and FIG. 14B shows the sling occlusive member in an occluding position.

DETAILED DESCRIPTION

Figure 1A:
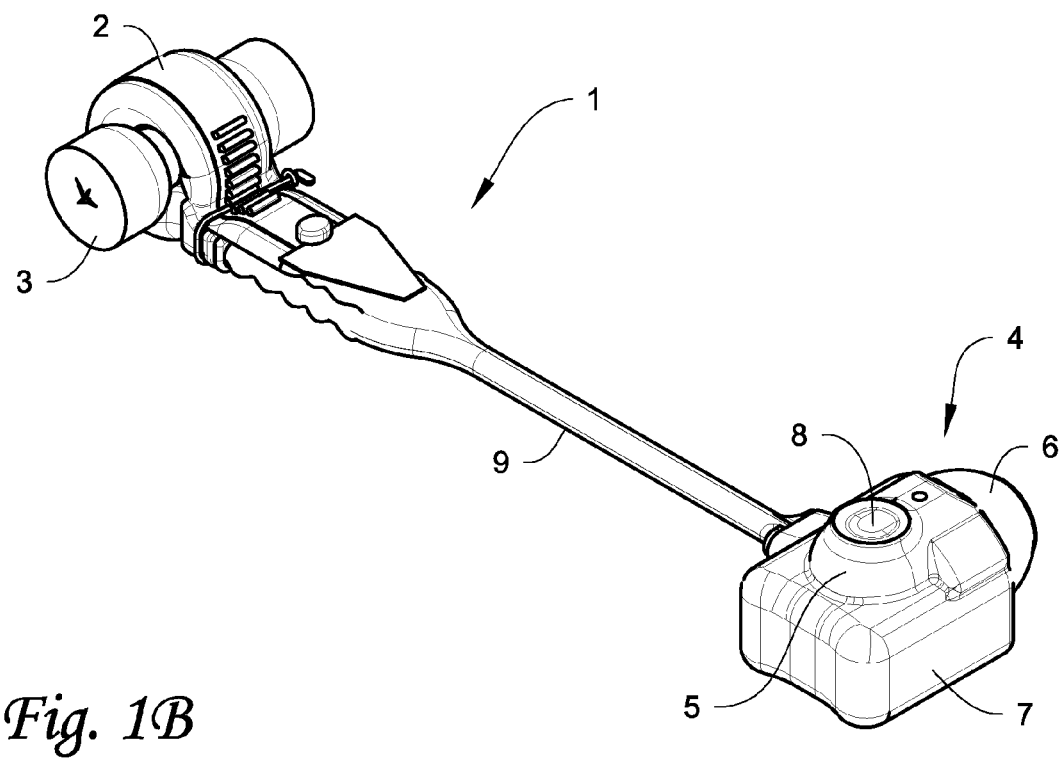
FIG. 1A is a perspective view of an embodiment of a mechanical occlusive device encircling a vessel in a closed activated state.

In the following detailed description, reference is made to the accompanying drawings which form a part hereof, and in which is shown, by way of illustration, specific embodiments in which inventive concepts may be practiced. These embodiments are described in sufficient detail to enable those skilled in the art to practice the invention, and it is to be understood that the embodiments may be combined or used separately, or that other embodiments may be utilized and that structural and procedural changes may be made without departing from the spirit and scope of the inventive concepts. The following detailed description provides examples, and the scope of the present invention is defined by the claims to be added and their equivalents.

It should be noted that references to "an," "one," or "various" embodiments in this disclosure are not necessarily to the same embodiment, and such references contemplate more than one embodiment.

The terms "above," "on," "under," "top," "bottom," "up," "down," "horizontal," and "vertical" and the like used herein are in reference to the relative positions of the vessel occlusive device, and its constituent parts, in use when oriented as in FIGS. 1-14.

In this document, the terms "occlude," "occluding," "occlusive" or "occlusion" respectively mean partially or completely occlude, partially or completely occluding, partially or completely occlusive, or partial or complete occlusion.

In this document, the terms "encircle," "surround" or "enclose" respectively mean partially or completely encircle, surround or enclose.

This document generally discusses, among other things, vessel occlusive devices and methods for occluding a vessel or vessels that convey fluid in humans and animals. As one particular example, the vessel occlusive devices and methods herein discuss applications that involve occluding a urethra by implanting an artificial device in a human body for providing an incontinent patient protection against urine leakage and for providing control over the patient's voiding function. However, it is to be understood that the present devices and methods may be employed in other areas, including, but not being limited to, fecal incontinence, gastro-esophageal reflux disease, and gastric banding for weight loss, bile duct flow control, male and/or female fertility control through reversible occlusion of the seminal vesicles or fallopian tube, or to provide general occlusion or support of body vessels for other purposes. Generally, it will be appreciated that the discussion below can apply to various vessels and/or body parts that can convey fluid and may have a need to be restricted or occluded by an occlusive device. It is also to be understood that the occlusive devices described herein may include multiple pieces or components operatively connected to each other, and that they may be either partially or entirely implantable in the body of humans or animals.

Vessel occlusive devices as described herein generally include an occlusive member and a control mechanism for actuating the occlusive member into occluding and non-occluding positions. The occlusive member can be configured to apply a constant force on a targeted vessel when the occlusive member is actuated in the occluding position.

Methods for controlling fluid flow in a fluid conveying body vessel include implanting a vessel occlusive device inside the body of a subject in need. The step of implanting may include surrounding at least a portion of the fluid conveying vessel and actuating the vessel occlusive device to apply an occlusive force and occlude the fluid conveying vessel. The occlusive force may be released when fluid flow is to be allowed through the fluid conveying vessel. The step of releasing occlusive force may include actuating the vessel occlusive device to a deactivated/non-occluding position. The vessel occlusive device may be then reactuated into the activated/occlusive position when fluid flow is no longer to be allowed. In one embodiment, a constant force can be applied on the fluid conveying vessel during at least one of the implanting and the reactuating steps.

Figure 1B:
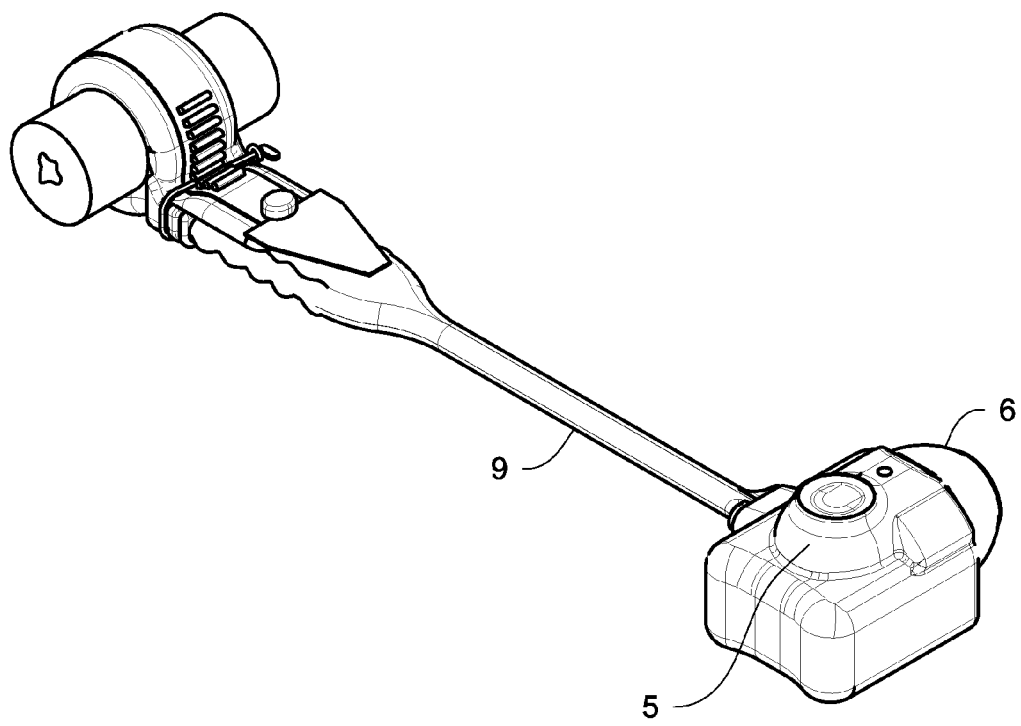
FIG. 1B is a perspective view of an embodiment of a mechanical occlusive device encircling a vessel in an open deactivated state.

An embodiment of the vessel occlusive device 1 for implantation in males is shown in FIGS. 1A and 1B. In one embodiment, the occlusive device 1 is implanted entirely and no pre- or post-implantation assembly is required. An occlusive member 2 may encircle a urethra 3. A control mechanism 4 may be connected to the occlusive member 2 through a conduit 9. The conduit 9 may be flexible to accommodate bodily movement by the human implant subject. In some embodiments, a portion of the conduit 9 may encircle a close wound metal coil structure (e.g. coil structure 15 described further below), which is flexible and can be bent.

The control mechanism 4 may have an activation button 5 and a deactivation button 6 that are encapsulated by a silicone boot 7 which may incorporate a needle port or septum 8. The control mechanism boot 7 may be infused through the septum 8 with normal saline or radiopaque solutions intended to allow visualization of the otherwise non-radiopaque occlusive member 2.

The occlusive device 1 may be implanted in the scrotum in males and the labia or abdominal wall in females. Before the implantation, the occlusive member 2 may be filled with a fluid and the occlusive member 2 may be configured to retain the fluid inside the occlusive member 2. The occlusive member 2 may be implanted in a deactivated/non-occlusive condition to a patient for approximately 6 weeks post-operatively to facilitate healing and allow pain and edema to subside. Following this period, the occlusive device may be activated by depressing an activation button 5 through the intact scrotal skin. In so doing, the occlusive member 2 may contract to apply a preset occlusive pressure, for example about 50-80 cm $H_2O$, to the urethra 3, which can occlude the urethra 3. The patient is then free to depress a deactivation button 6 to release the tension of the occlusive member 2 and cause the occlusive member 2 to return to the deactivated/non-occlusive condition, and allow unobstructed voiding. To re-establish urethral occlusive pressure and continence, the patient can push the activation button 5 again.

Figure 2A:
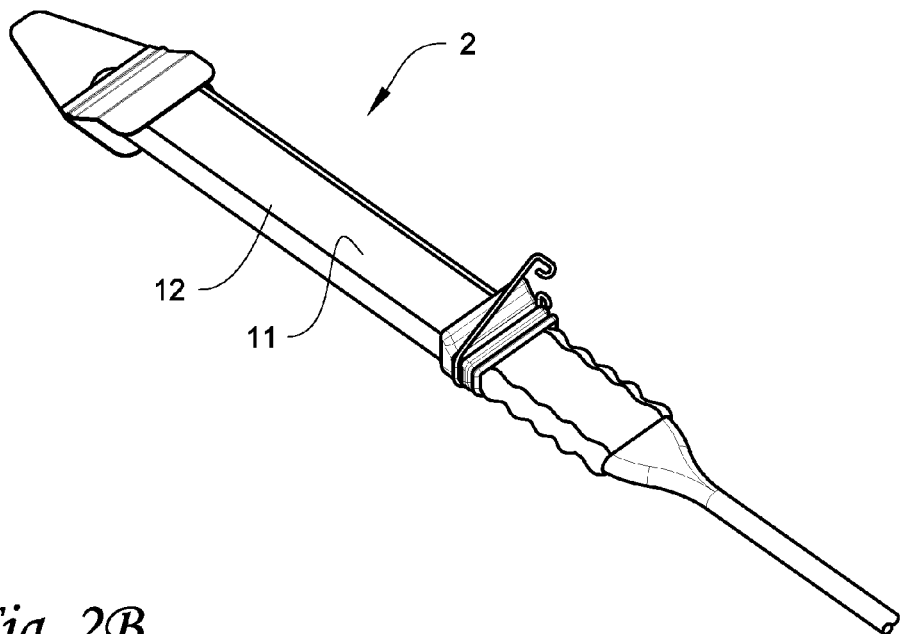
FIGS. 2A and 2B are perspective views of an occlusive member of an occlusive device.
Figure 2B:
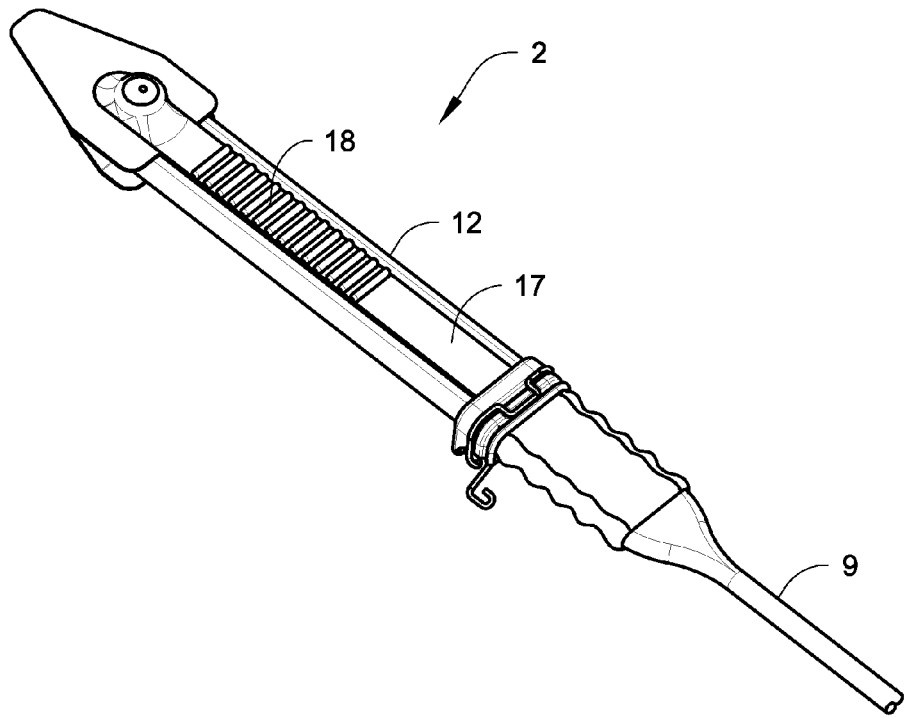

An embodiment of the occlusive member 2 is shown in FIGS. 2A and 2B in its extended condition prior to implantation. The occlusive member 2 may have an outer sheath 12 that is connected to conduit 9. The outer sheath 12 may have a thin wall structure. The thin wall structure may be flexible and elastic. The outer sheath 12 may generally have two surfaces: inner surface 11 and outer surface 17. The inner surface 11 of the outer sheath 12 may be flat and configured to be in contact with a body vessel such as a urethra when in use. The inner surface 11 can contract the body vessel when in use. The outer surface 17 of the outer sheath 12 may be configured to be away from the body vessel when in use. The outer surface 17 may be configured to have a flexible sizing band with locking detents 18 situated along the length of the outer sheath 12, which may be used to size the occlusive member 2 to fit a specific vessel circumference encountered during implantation (see below for more detail).

Figure 3A:
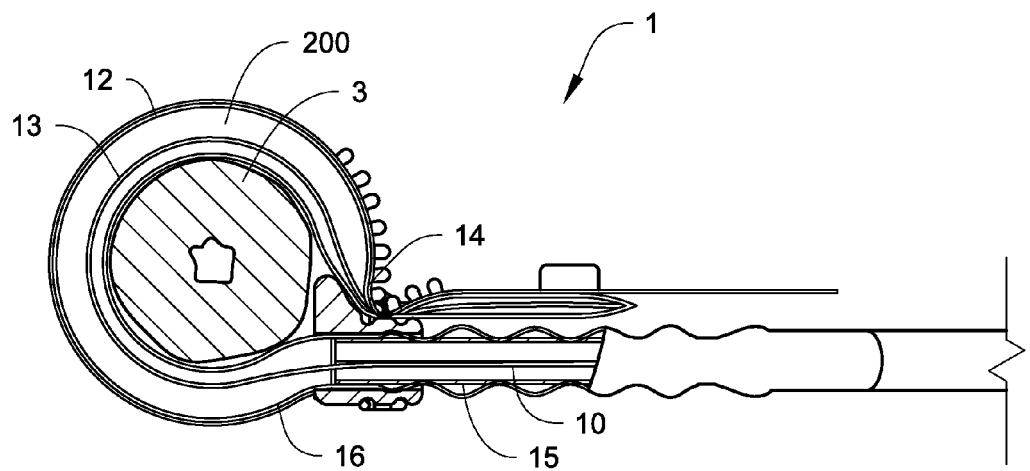
FIG. 3A is a partial side cross-section view of an embodiment of an occlusive member encircling a vessel that is in an open deactivated state.
Figure 3B:
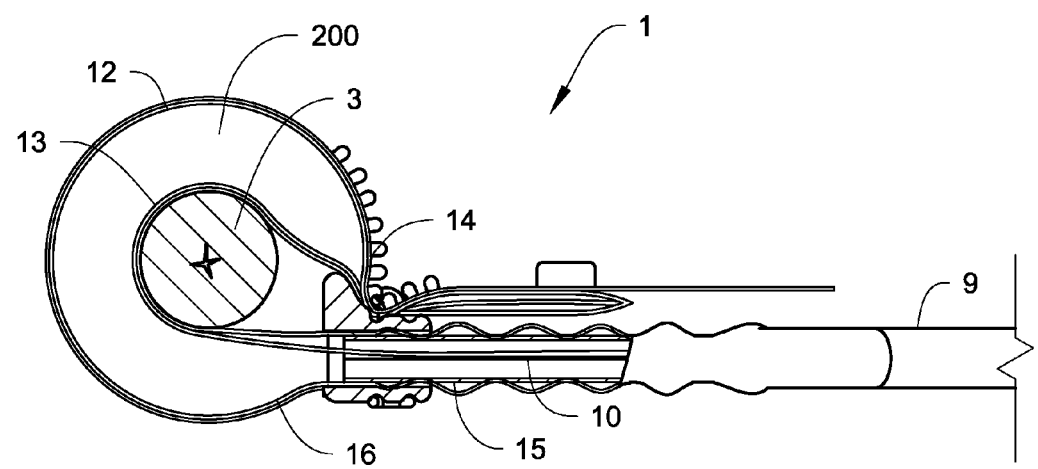
FIG. 3B is a partial side cross-section view of an embodiment of an occlusive member encircling a vessel that is in a closed activated state.

As shown in FIGS. 3A and 3B, when implanted, the outer sheath 12 of the occlusive device 1 may encircle a urethra 3. The outer sheath 12 may have a space 200 inside the outer sheath 12. In one embodiment, the outer sheath 12 may be a tubular structure. An inner occlusive tape 13 is disposed through the outer sheath 12 in the space 200. One end of the inner occlusive tape 13 may be fixed to a terminal end 14 of the outer sheath 12, while the other end of the inner occlusive tape 13, proximal end 10 of the occlusive tape 13, may be free to translate back and forth inside the outer sheath 12 relative to a proximal end 16 of the outer sheath 12. When a tension is applied to the proximal end 10 of the inner occlusive tape 13, the inner occlusive tape 13 can cause the outer sheath 12 to collapse along its length and presses the outer sheath 12 against the urethra 3 so as to occlude the urethra 3. The proximal end 16 of the outer sheath 12 may be connected to conduit 9 to provide a receptacle through which the inner occlusive tape 13 may be pulled. A flexible metal coil structure 15 may be connected to the proximal end 16 of the other sheath 12. The coil structure 15 may also extend into the conduit 9. The coil structure 15 is flexible and can be bent to allow the occlusive device 1 to conform to anatomical variants and to flex and bend freely with bodily movement. The proximal end 10 of the inner occlusive tape 13 may go through the coil structure 15. The coil structure 15 may be a closed wound structure to provide axial structural stiffness. The stiffness of the coil structure 15 may prevent compression of the inner occlusive tape 13 by the surrounding bodily tissues, which may hinder movement of the inner occlusive tape 13. The conduit 9 and the outer sheath 12 may be configured to be water tight. The conduit 9 may be in fluid communication with the space 200 so that a liquid may flow between the conduit 9 and the space 200.

The internal space 200 may be air-filled as received prior to implantation. Placing an air-filled, closed structure within the body can create an osmotic pressure gradient across the membrane of the structure. If the membrane is permeable or semi-permeable as most thermoplastic and thermoset materials are, there can be a net loss of air within the structure and a vacuum may be created. This vacuum may cause collapsing deformable, sealed structures within the body and a similar collapse in an occlusive structure may prevent intended function. Therefore, prior to implantation, the internal space 200 may be filled with an isotonic medium such as normal saline or isotonic radio-opaque solution intended to aid in radiographic visualization of the implanted device. Filling the internal space 200 with an isotonic medium may also prevent fluid exchange between the internal space 200 and the surrounding body tissue when in use.

The occlusive device 1 may have two states when in use: a deactivated/non-occlusive state and an activated/occlusive state. In the deactivated state, there is no tension applied to the proximal end 10 of the inner occlusive tape 13. As a result, the inner occlusive tape 13 cannot press the outer sheath 12 and cannot occlude the urethra 3. In an activated state, a tension is applied by a control mechanism (e.g. control mechanism 4), which is connected through the conduit 9 to the proximal end 10 of the inner occlusive tape 13. This tension draws the proximal end 10 toward the control mechanism. As a result, the outer sheath 12 collapses along its length, and therefore presses against the urethra 3 so as to occlude the urethra 3. Because the space 200 may be filled with a liquid, when the outer sheath 12 collapses along its length in the activated state, the shape of a cross section of the outer sheath 12 may change.

Figure 4A:
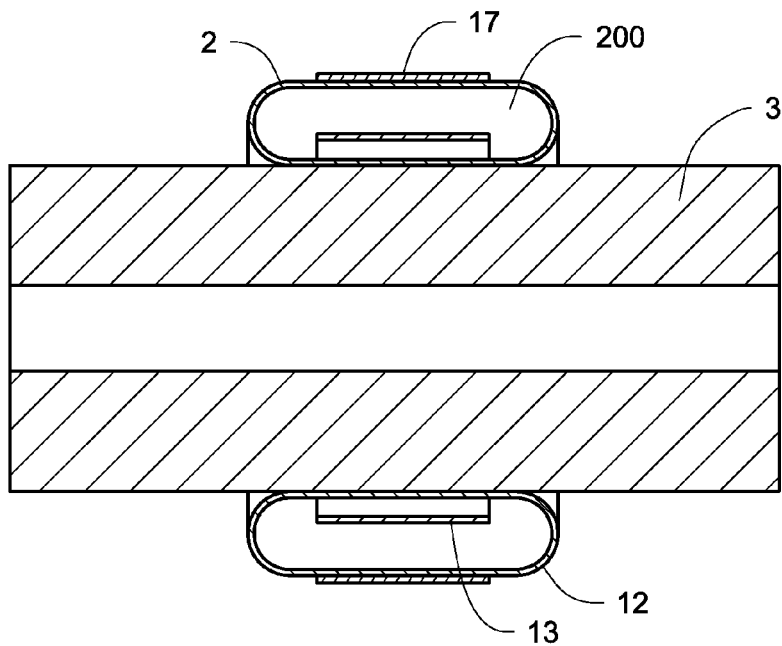
FIG. 4A is a front cross-section view of an embodiment of an occlusive member encircling a vessel that is in an open deactivated state.
Figure 4B:
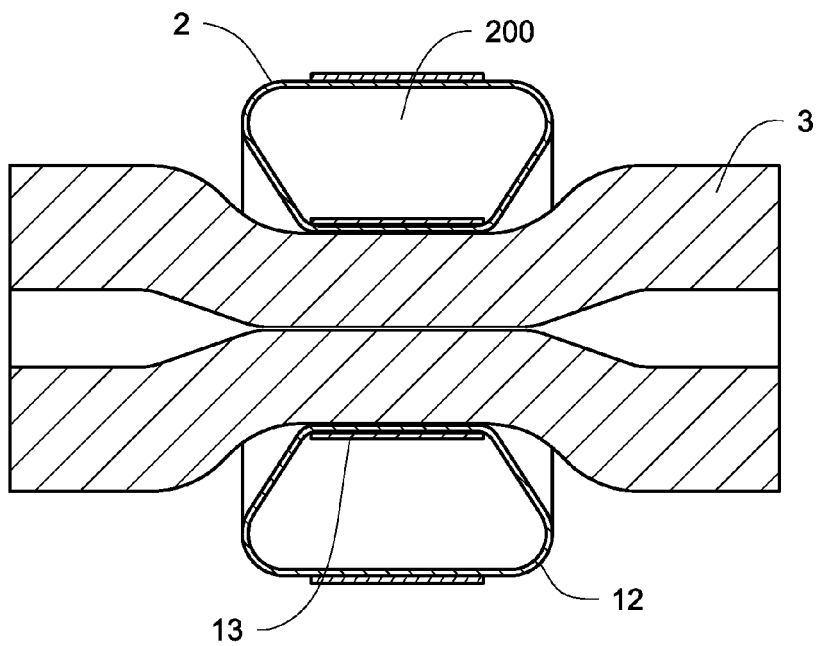
FIG. 4B is a front cross-section view of an embodiment of an occlusive member encircling a vessel that is in a closed activated state.

Referring to FIGS. 4A and 4B, the deactivated and activated states and the change of the shape of the cross section of the occlusive member 2 including the outer sheath 12 are further illustrated. As shown in FIG. 4A, when there is no tension applied to the inner occlusive tape 13, the occlusive device is in the deactivated state, and the outer sheath 12 may not have enough pressure to occlude the urethra 3. Therefore, the urethra 3 is open and allows a fluid to flow through. When a tension is applied to the inner occlusive tape 13, the device is in an activated state, and the outer sheath 12 may collapse along its length as shown in FIG. 3B, which also leads to the shape of the cross section of the space 200 of the outer sheath 12 to change (as shown in FIG. 4B) compared to the shape of the deactivated state as shown in FIG. 4A. As a result, the outer sheath 12 may be pressed against the urethra 3 by the occlusive tape 13 so as to occlude the urethra 3 and prevent fluid flowing through the urethra 3.

The outer surface 17 of the outer sheath 12, which is opposite to the surface of the outer sheath 12 that contracts the urethra 3, may be configured to have a flexible sizing band. The sizing band may encircle the entire length of the outer sheath 12, or it may encircle only a portion of the outer sheath 12.

The outer sheath 12 may be made of a thin resilient member so that the outer sheath 12 may return to the shape of the deactivated state when the tension applied to the inner occlusive tape 13 in the activated state is released. The outer sheath 12 may be flexible so that it does not hinder the ability of the inner tape 13 to compress the urethra 3 under a tension.

The inner occlusive tape 13 may be constructed from expanded polytetrafluoroethylene (ePTFE) with an internodal distance (porosity) of <30 μ and the tape 13 may have a thickness within the range of 0.010" to 0.025" and a width of 7 mm to 10 mm. The length of the tape 13 may be sufficient to encircle urethras within the range of 3.0 cm to 5.5 cm. The outer sheath 12 may also be constructed from ePTFE so as to allow movement of the inner occlusive tape 13 through the outer sheaths 12 with minimized frictional resistance. The outer sheath 12 may also be coated with a thin, pliable layer of silicone, polyurethane or other thermoplastic or thermoset material on its surface to prevent the movement of bodily fluids and bacteria into the interior of the device and to prevent tissue ingrowth into the pores of the outer sheath 12. The outer sheath 12 may have an internodal distance and wall thickness within the same ranges as the inner occlusive tape 13. However, the width of the tubular outer sheath 12, when laid flat, may be generally greater than the width of the inner occlusive tape 13 to allow the outer sheath 12 to collapse to a small enough diameter to occlude the urethra 3 which it encircles, as shown in FIGS. 4A and 4B.

Figure 5:
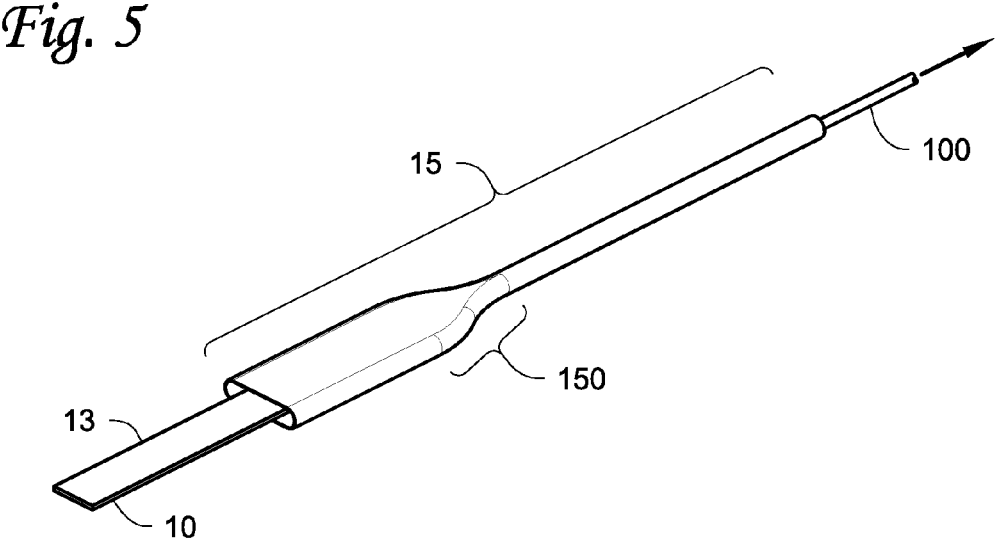
FIG. 5 is a perspective view of a portion of an embodiment of an occlusive member showing a coil and an inner occlusive tape.

Referring to FIG. 5, one embodiment of the coil structure 15 and the occlusive tape 13 are illustrated. For clearer illustration, the coil windings of the coil structure 15, which winds around a longitudinal axis of the occlusive tape 13, are not shown. The longitudinal axis runs through the proximal end 10 of the occlusive 13 toward the control mechanism (the arrow in FIG. 5 illustrates the direction toward the control mechanism). As shown in FIG. 5, the cross section of the coil structure 15 may vary along its length to provide an appropriate combination of flexibility/stiffness and geometry shape into which the geometry of the inner occlusive tape 13 may be accepted. One such geometric variant may be a rectangular cross-section appropriate to accept at least a portion of the proximal end 10 of the flat inner occlusive tape 13 which transitions into a circular cross-section through which a cable 100 joining the inner occlusive tape 13 to a control mechanism may pass. The coil structure 15 may have a transitional section 150 between the portion of the rectangular cross-section and the portion with the circular cross-section. The circular cross-section portion may be more uniformly flexible in all directions than the rectangular cross-section portion. This may enable the control mechanism to be placed more freely during the implantation procedure. Many other geometric variations may also be employed.

Figure 6A:
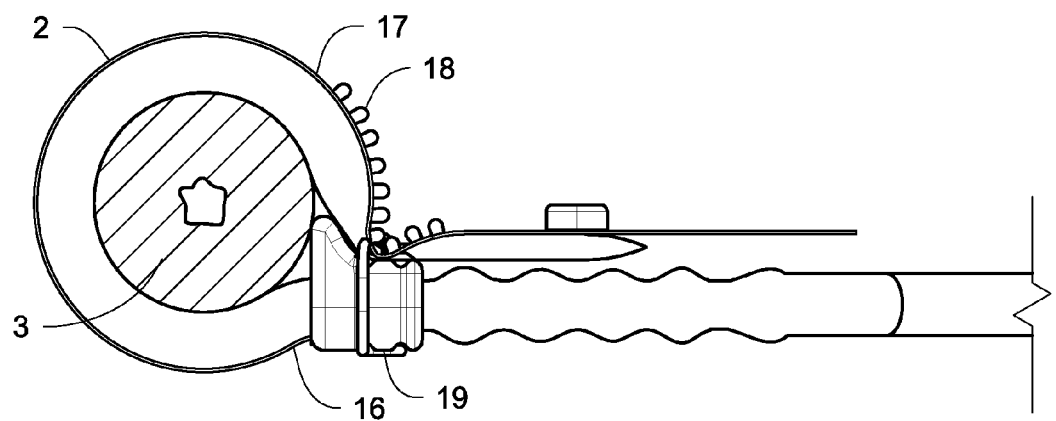
FIGS. 6A and 6B are side views of an embodiment of an occlusive device.
Figure 6B:
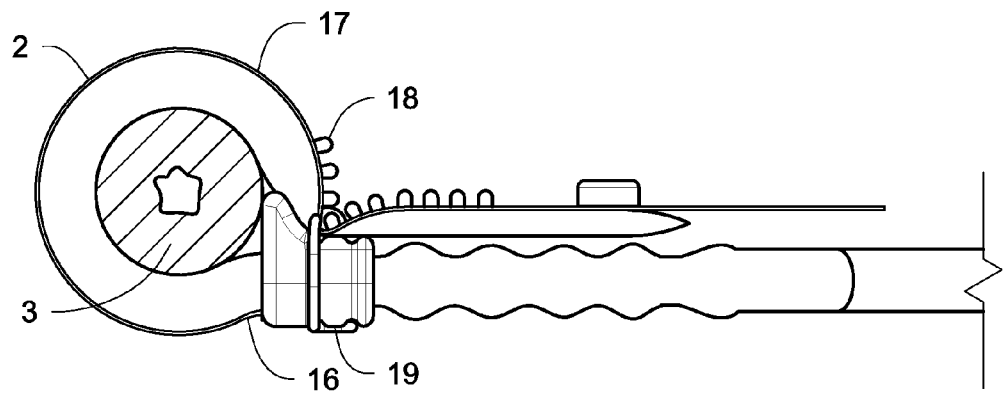
Figure 7A:
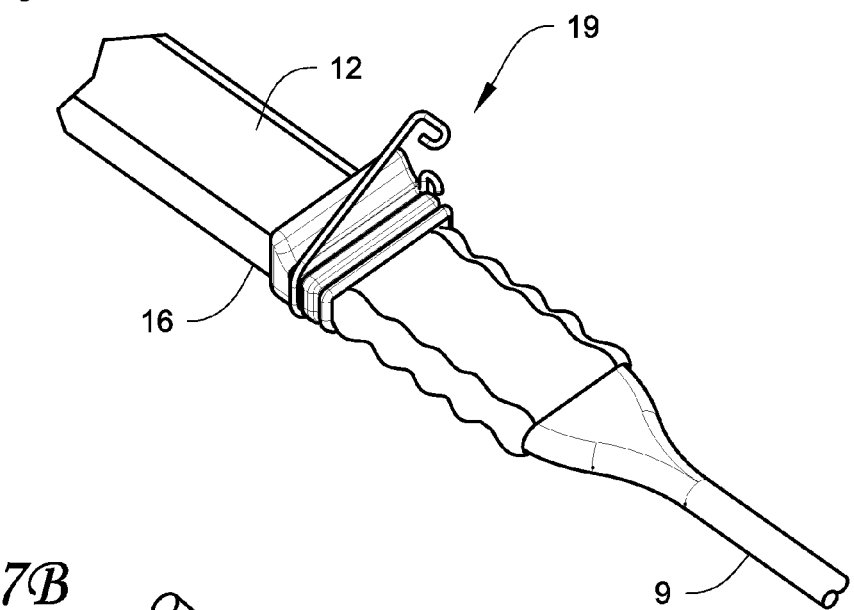
FIGS. 7A and 7B are perspective views of portions of an occlusive device.
Figure 7B:
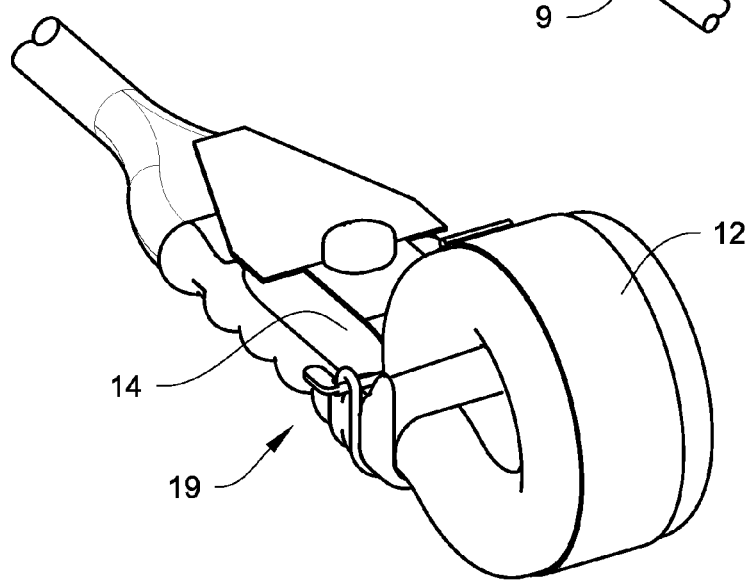

Another embodiment of the occlusive device provides a means by which the occlusive member 2 may be sized to a specific urethral circumference encountered during implantation. In such circumstance, there may be no need to measure the urethra at the time of implantation and select from a wide variety of devices sized for specific urethral circumference ranges. As shown earlier in FIG. 2B as well as in FIGS. 6A and 6B herewith, the outer surface 17 of the occlusive member 2 may be have a flexible sizing band with a plurality of locking detents 18 situated along its length. When the occlusive member 2 is placed during the implantation procedure, a portion of the occlusive member 2 may be conformed to encircle the urethral surface. To ensure that the portion of the occlusive member 2 fits as closely as possible to the urethra 3 and prevents the occlusive member 2 from being released from this position following implantation, a metal clip 19 that is attached to the occlusive member 2 near the proximal end 16 of the outer sheath may engage the locking detent(s) 18 of the flexible sizing band. The clip 19 may be locked in place to maintain a predetermined circumference encircled by the occlusive member 2 during the implantation. By positioning the clip 19 to engage a different locking detent, the circumference of the portion of the occlusive member 2 that conformed to encircle the urethral surface may be adjusted One embodiment of the clip 19 and locking mechanism is depicted in FIGS. 7A and 7B. FIG. 7B (as well as FIG. 1A) shows the clip 19 in a closed or locked position. FIG. 7A shows the clip 19 in an open position. The clip 19 may be positioned close to the proximal end 16 of the outer sheath 12 that is connected to the conduit 9. The clip 19 may have an integral spring biased to holding the clip 19 in its locked position. Alternately, the clip 19 may be hinged on one end to facilitate easy opening during the implantation procedure. The terminal end 14 of the outer sheath 12 may pass underneath the clip 19 and the clip 19 may be locked during an implantation procedure. Further, locking the clip 19 in place also serves to fix the portion of the inner occlusive tape that is enclosed by the terminal end 14 of the outer sheath 12 to the terminal end 14 as shown in FIGS. 3A and 3B. The inner occlusive tape 13 within the outer sheath 12 is still free to move relative to the outer sheath 12 from the clip 19 to the proximal end of the inner occlusive tape, as shown in FIGS. 3A and 3B.

The flexible sizing band may be molded from implant grade silicone rubber of sufficient durometer (30-80 durometer) to prevent deformation of the locking detents 18 in use. Polyurethane or other flexible, biocompatible thermoplastics or thermoset materials may be used as a substitute for silicone rubber. The clip 19 may be wound 316L stainless steel, MP35N (Nickel-Cobalt alloy) wire or other biocompatible, rigid thermoplastic or metal. The coil 19 may be covered by silicone coated thin walled ePTFE or molded silicone sheath conforming to the coils geometry to prevent the incursion of bodily fluids and tissue ingrowth into the occlusive device's interior.

When encircling the urethra 3, an axial tension applied to the inner occlusive tape 13 by the control mechanism can apply a pressure to the urethra 3. The pressure applied to the urethra 3 is affected by the surface area of the inner occlusive tape 13 contracting the urethra 3 and the axial tension applied to the inner occlusive tape 13 by the control mechanism. The pressure applied to the urethra 3 by the inner occlusive tape 13 may be characterized by the LaPlace relationship which allows calculation of pressures generated in cylindrical bodies as follows:

$$P = T/RW$$

where P=pressure within the cylindrical body (urethra)
T=tension applied circumferentially about the urethra
R=Radius of the urethra
W=Width of the tensioning member as measured along the axis of the urethra From this equation, it must be noted that when the width of the occlusive tape is constant, for equal tension T circumferentially applied to the urethra, a smaller urethral circumference can result in a higher urethral pressure P within the cylindrical body of the urethra and larger urethral circumferences can result in lower urethral pressures P. It has been demonstrated that the range of urethral circumferences found in men who are candidates for implantation is from about 3.5 cm to about 4.5 cm. Using a tape design with a single constant width for this circumferential range may cause urethral pressures to fall outside of the pressure range of about 50-80 cm H$_2$O that is required to occlude the urethra effectively if the urethral circumference is large.

Figure 8:
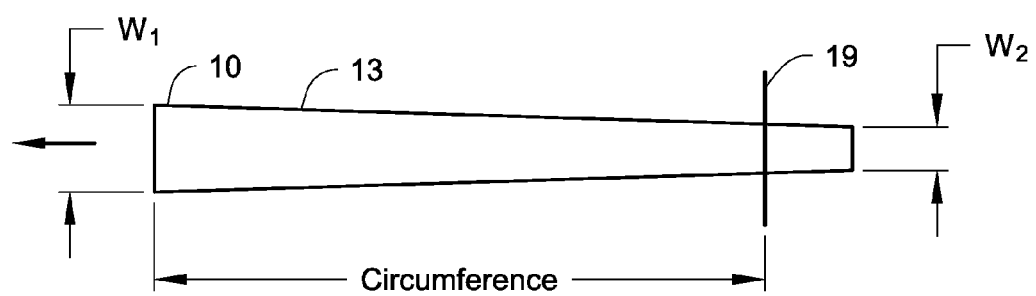
FIG. 8 is a side view of an embodiment of an inner occlusive tape.

To minimize the pressure variation due to the difference in the urethral circumference, as shown in FIG. 8, the occlusive tape 13 may generally incorporate a varied width along the length of the tape 13. In one embodiment, the width of the tape 13 may have a tapered profile, which has width $W_1$ and $W_2$ at the ends of the occlusive tape 13 respectively and $W_1$ is larger than $W_2$, In one embodiment, the proximal end 10 of the occlusive tape 13 that is connected to the control mechanism (the arrow in FIG. 8 shows the direction leading to the control mechanism) has the width $W_1$. When sizing the occlusive member 2 as shown in FIG. 6A to accommodate a larger urethra circumference, the locking clip 19 is shifted toward the thinner end of the tape 13 ($W_2$). This effectively decreases the composite width of the tape 13 and increases the urethral pressure. When sizing the occlusive member 2 as shown in FIG. 6B to accommodate a smaller urethra circumference, the locking clip 19 is shifted toward the wider end of the tape 13 ($W_1$). This effectively increases the composite width of the tape 13 and decreases the urethral pressure. Experimental data suggests that a tape width range ($W_1$ to $W_2$) of about 10 mm to about 3 mm can provide the appropriate urethral pressures.

Figure 9:
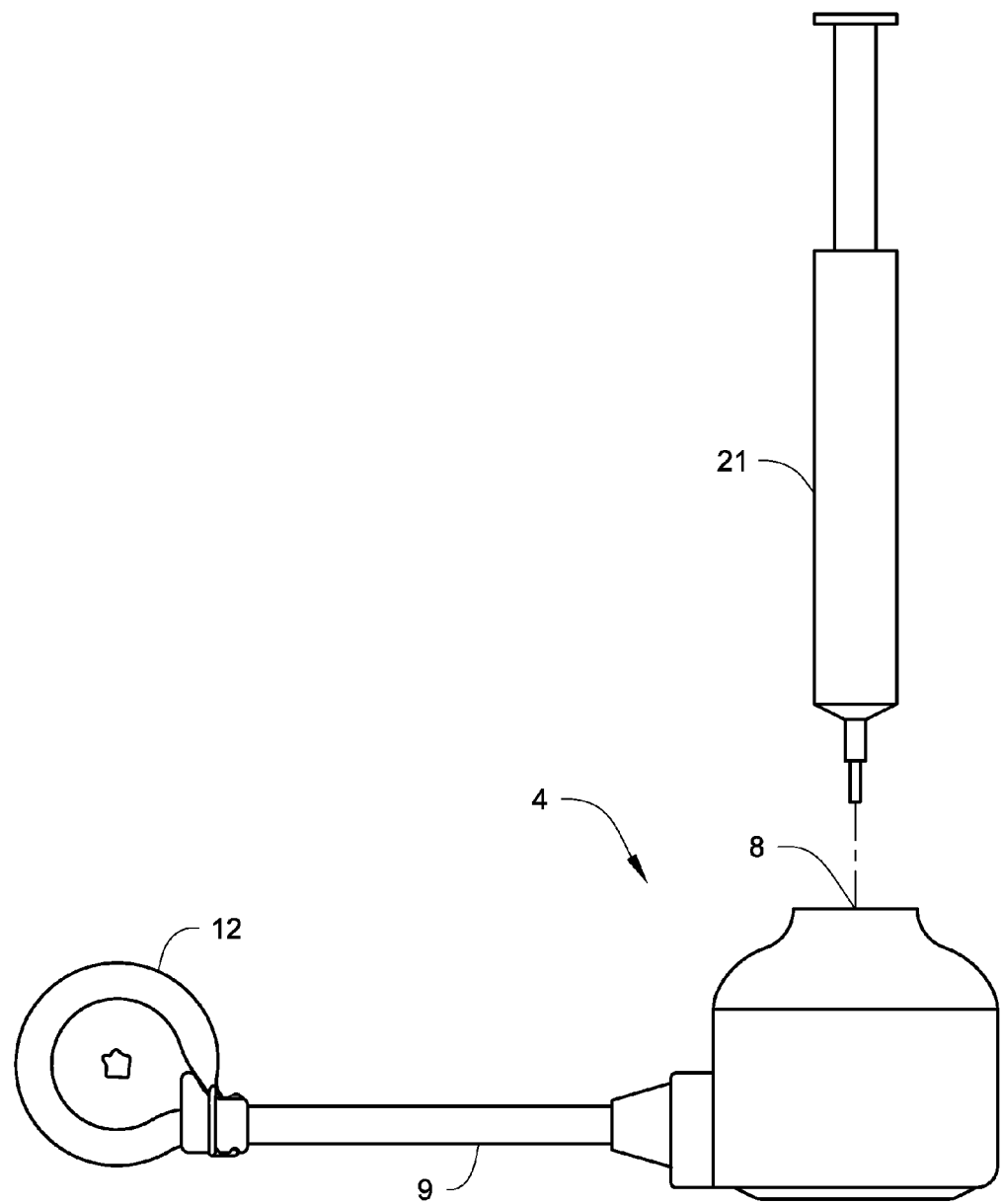
FIG. 9 is a side elevation view of an embodiment of an occlusive device and a syringe.

As discussed earlier and shown in FIG. 9, the outer sheath 12 may be filled with a liquid before implantation. To fill the outer sheath 12, a small hypodermic needle (for example, a 21-23 Gauge needle) attached to a saline filled syringe 21 may be inserted through a septum 8 of a control mechanism 4 as seen in FIG. 9. In some embodiments, the internal of the control mechanism 4, the conduit 9 and the outer sheath 12 are in fluid communication; therefore the saline solution can flow into the outer sheath 12 through conduit 9.

Figure 10A:
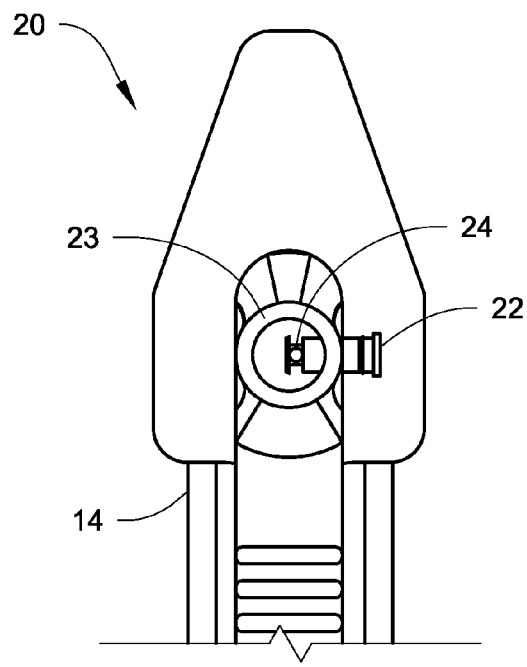
FIGS. 10A and 10B are front views of a bleed valve that is connected to one end of an occlusive member.
Figure 10B:
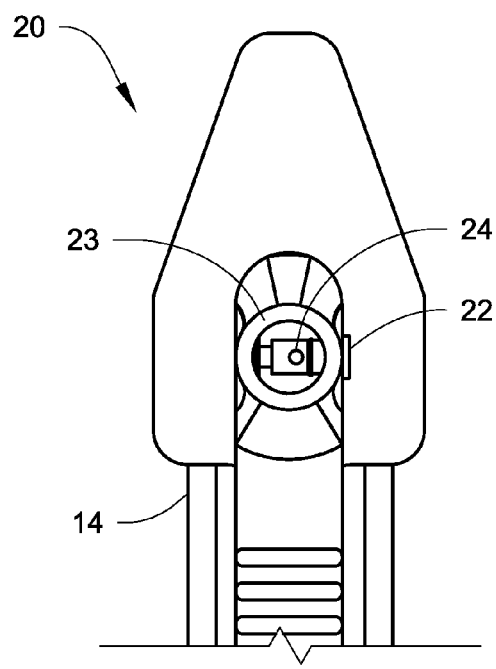

Now refer to FIGS. 10A and 10B, an embodiment of a bleed valve 20 that can be used to facilitate the liquid filling of the outer sheath is described. The bleed valve 20 may be incorporated into the terminal end 14 of the outer sheath of the occlusive member and may also be integral to the molded flexible sizing band affixed to the occlusive member. The space 200 of the outer sheath 12 as shown in FIG. 3A may be in fluid communication with the bleed valve 20 as shown in FIGS. 10A and 10B. A metal spool valve 22 may be inserted into the body 23 of the bleed valve 20 and may be configured to allow air to escape from the space 200 of the outer sheath 12 as shown in FIG. 3A through a bleed valve port 24 as seen in FIG. 10A. When a liquid is injected into the space 200 through the septum 8 as shown in FIG. 9, air inside the space 200 can escape through the bleed valve port 24 as shown in FIG. 10A, When all air has been removed from the space 200, the liquid can be seen to leak from this open bleed valve port 24. The needle may then be removed from the control mechanism 4 and the spool valve 22 may be depressed to insert it fully within the body 23 of the bleed valve 20 as seen in FIG. 10B. This action can seal the bleed valve port 24 to prevent the further leakage of solution from or leakage of air back into the outer sheath 12.

The spool valve 22 may be machined or molded from a wide variety of materials including 316L stainless steel, MP35N (Nickel-Cobalt alloy) wire or other biocompatible, rigid thermoplastic or metal. The body 23 may be molded of a resilient material such as silicone rubber. The mating channel of the body 23 may be of a smaller diameter than the spool valve 22 to form a compressive air tight and water tight seal between the two structures.

Movement and the tension applied to the occlusive member may be generally supplied by a control mechanism implanted in the scrotum of the male or in the abdominal wall of the female or in a miniaturized version within the labia of the female. Generally, depression of an activation button on the control mechanism through the intact skin may cause a spring force to retract the occlusive member and apply a constant pressure to the urethra which it encircles. Depression of a deactivation button that may be also located on the control mechanism may release the spring force from the occlusive member and removes pressure from the urethra.

Embodiments of various control mechanisms are described in great detail in U.S. Pat. No. 8,007,429 VESSEL OCCLUSIVE DEVICE AND METHOD FOR OCCLUSING A VESSEL. One of these embodiments is described below.

Figure 11A:
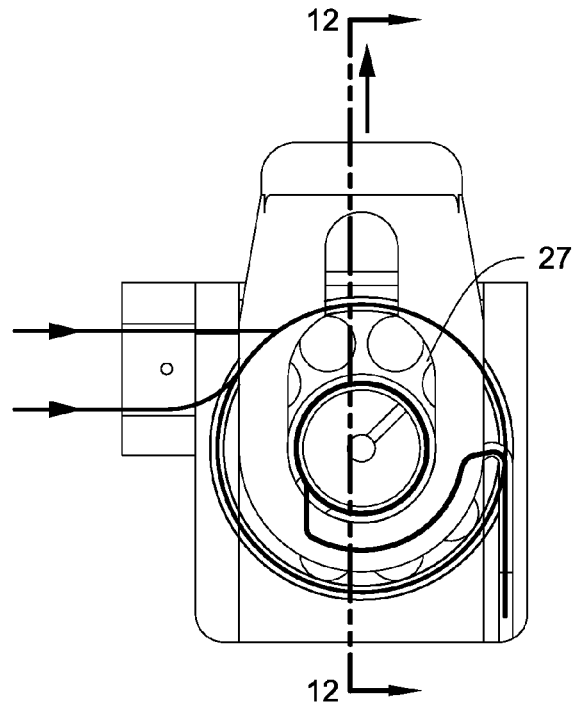
FIGS. 11A and 11B are elevation views of a control mechanism.
Figure 11B:
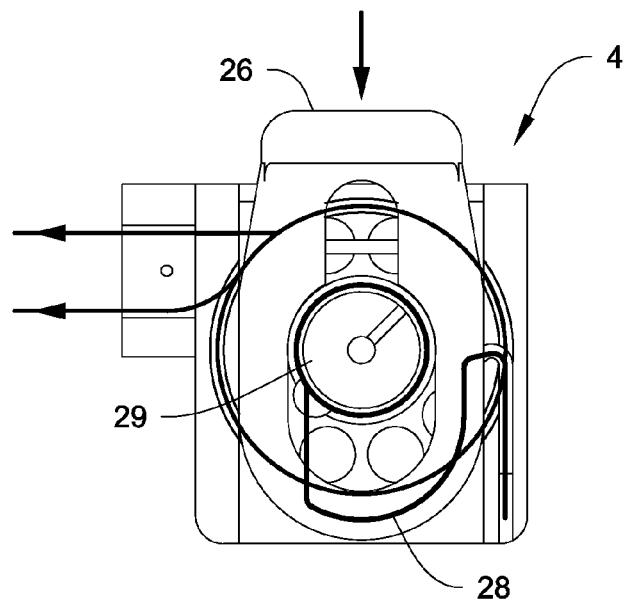

As shown in FIGS. 11A and 11B, a cable and pulley system may be used as a control mechanism. The pulley 27 may rotate counter clockwise when a user depresses a deactivation button 26 exiting the control mechanism 4. A cable 28 may wrap around a small pulley 29 at one end and the circular base of the deactivation button 26 at its other end as shown in FIGS. 11A and 11B. As the deactivation button 26 advances, the distance that the cable 28 can be pulled can be doubled relative to the distance that the deactivation button 26 is depressed.

Figure 12A:
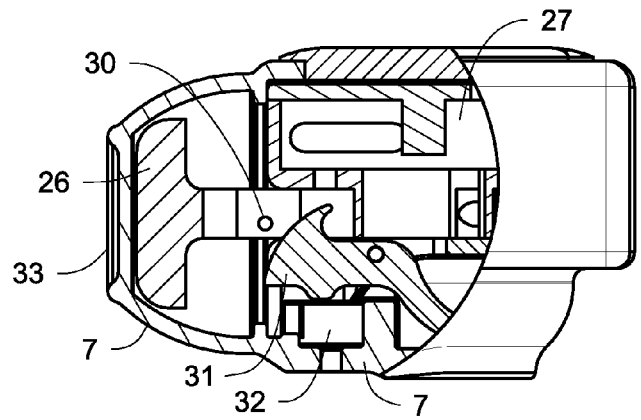
FIGS. 12A to 12C are partial sectional views of an embodiment of a control mechanism, and including a plunger dome as part of the cover of the control mechanism.
Figure 12B:
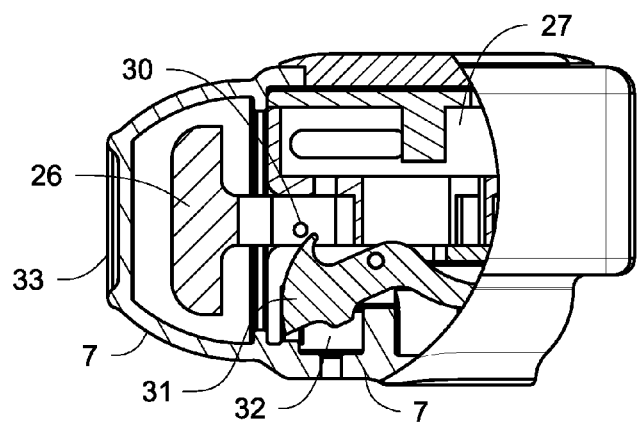
Figure 12C:
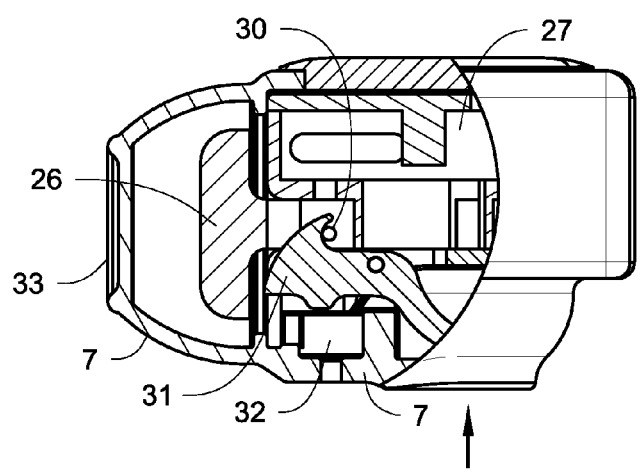

FIGS. 12A, 12B and 12C show side sectional views of the control mechanism as shown in FIGS. 11A and 11B. Particularly, an embodiment of a boot or cover 7 for at least the deactivation button 26 is illustrated, and a lever 31 and a détente pin 30 are also illustrated. When the deactivation button 26 is depressed to its full extent, The détente pin 30 contained within the deactivation button 26 can engage the lever 31, which may prevent the deactivation button 26 from returning to its original extended position. The lever 31 may be biased by a spring 32 captured between the lever 31 and a silicone rubber boot 7 surrounding the control mechanism. As the deactivation button 26 is depressed, the deactivation button dome 33 of the flexible silicone boot 7 may deform with the force applied to it, but may rebound to its original shape when the force is removed. In this way, the occlusive sheath may be held in a condition which does not compress the urethra. Rebounding of the dome 33 may prevent the tissue capsule, which normally forms around any implanted device, from restricting movement of the deactivation button 26.

When the patient desires to return to a continent state with the urethra compressed, the silicone boot 7 may be depressed over the lever 31 as shown in FIG. 12C (the arrow in FIG. 12C shows the direction of the depression). This can disengage the lever 31 from the détente pin 30, allowing the deactivation button 26 to return to an extended position under the bias of a constant force spring 34 nested within the pulley 27.

Figure 13:
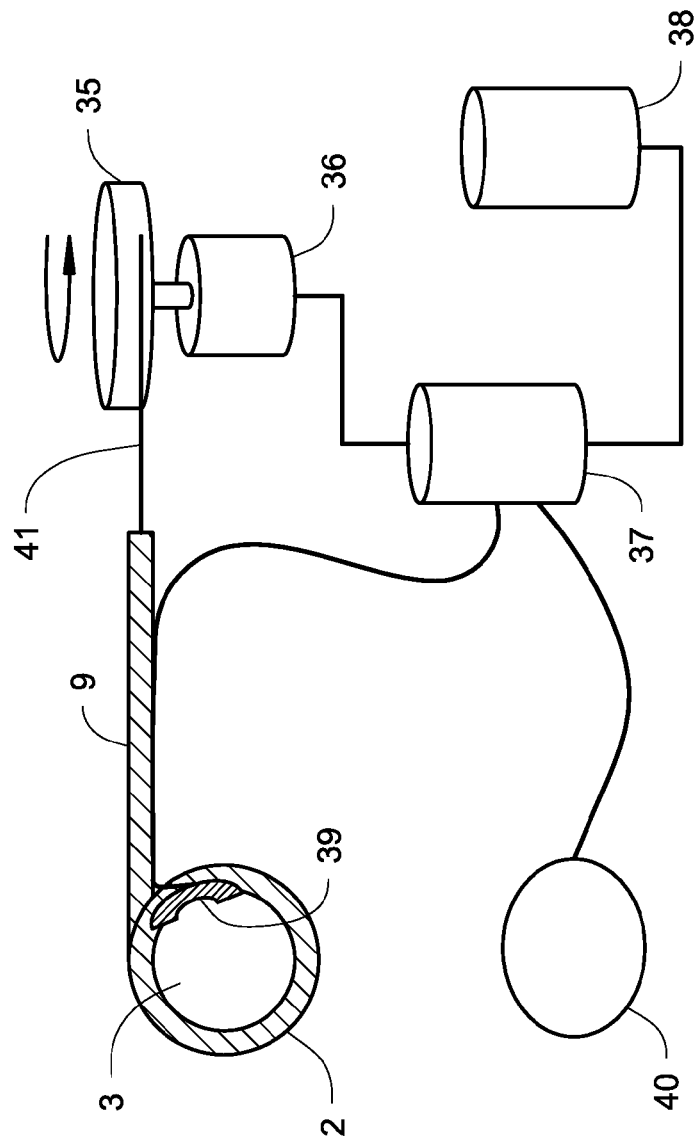
FIG. 13 is a schematic view of a motorized vessel occlusive device.

With reference to FIG. 13, the mechanical control mechanism 4, described above, may be configured as a closed loop, electro-mechanical, and servo-control system. This system may include an occlusive member 2 and a conduit 9 connected to the occlusive member 2, a pulley 35, a rotary actuator such as a motor 36, a micro-processor based control mechanism 37, a power supply 38 and separate urethral 39 and abdominal 40 pressure sensing elements. In this embodiment, the rotary actuator 36 may turn the pulley 35 which in turn may take up and apply load to a traction sutures 41 to occlude the urethra 3. It is appreciated that a linear actuator such as a lead screw may be used in place of a rotary actuator.

In a resting state, the pulley 35 may be biased so that the occlusive tape 2 applies about 0 to about 20 cm $H_2O$ pressure to the urethra. This pressure range is generally adequate to prevent urinary leakage during normal, unstressful activities. Urethral pressure may be continuously or intermittently monitored by a urethral pressure sensing element 39 situated between the occlusive member 2 and the outer surface of the urethra 3. Abdominal or bladder pressure may be monitored continuously or intermittently by a pressure sensor 40 implanted within the abdominal cavity, within the abdominal wall, within the bladder and/or within the bladder wall.

As bladder filling occurs, bladder pressure can increase within the range of about 20-60 cm $H_2O$. Sensing this pressure increase, the abdominal/bladder pressure sensor 40 may signal the control mechanism 4 to turn the motor 36 on and cause the pulley 35 to rotate and affect a rise in urethral pressure. When the urethral pressure sensing element 39 detects that urethral pressure is about 60-80 cm $H_2O$, the motor 36 may be turned off and the pulley 35 may be held in position to prevent any further pressure increase or decrease. Once the abdominal/bladder pressure reduces to about 20 cm $H_2O$ or less, the control mechanism 4 may again signal to allow the rotary actuator 36 to reverse the direction and reduce the tension on the traction sutures 41 until urethral pressures between about 0 and about 20 cm $H_2O$ are achieved.

Stressful events such as coughing, sneezing, laughing, etc. can often cause abdominal/bladder pressures spikes in excess of 60 cm $H_2O$. Pressure rise times of 35 msec and elevated pressure durations of approximately 100 msec have been recorded.

Sensing these pressure levels, the control mechanism 4 may cause the rotary actuator 36 to turn on and rotate the pulley 35 to affect a rise in urethral pressure of as much as 120 cm $H_{20}O$. When abdominal/bladder pressure declines to about 20 cm $H_2O$ or less, the control mechanism 3 allows the rotary actuator 36 to reverse direction and reduce tension on the traction sutures 41 until urethral pressures between about 0 and about 20 cm $H_2O$ are achieved.

When the user wishes to void urine, a switch may be manually activated through the skin. This action can cause the pulley 34 to free-wheel, reducing traction suture 41 tension until a 0 cm $H_2O$ urethral pressure is achieved, The user then voids urine through the unobstructed urethra 3. The user may then manually depress the switch again to return the device to its resting mode or the device will be programmed to automatically return to its resting mode within 3-5 minutes.

Figure 14A:
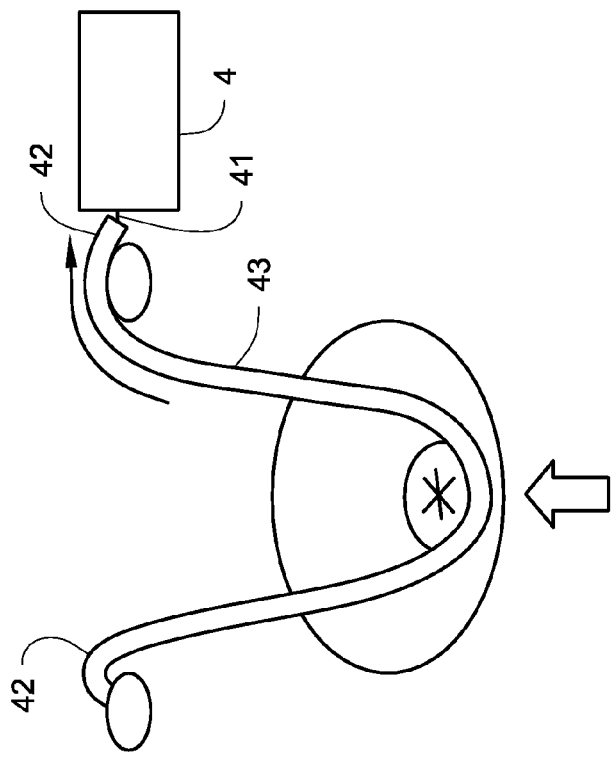
FIGS. 14A and 14B are schematic views of an embodiment of an occlusive device having a sling occlusive member.
Figure 14B:
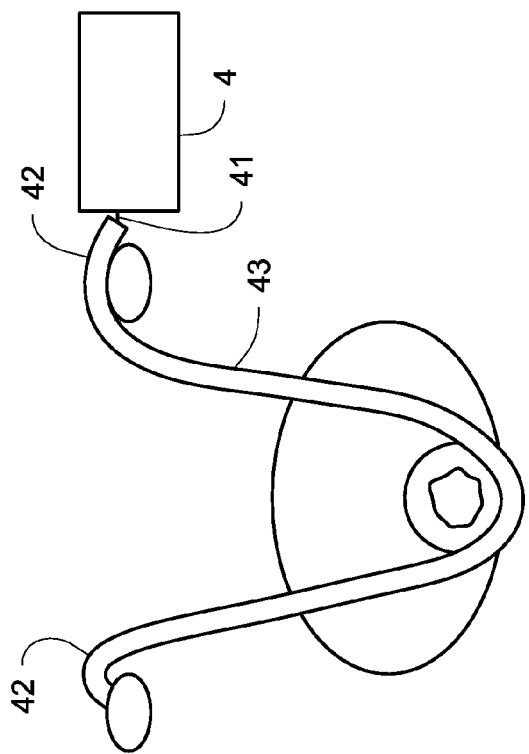

With the reference to FIGS. 14A and 14B, the occlusive device may also be configured to provide adjustable support to tubular body organs without totally encircling them. An example of this usage may be a sling configuration of the occlusive tape 43 to provide urethral support in both males and females. In this configuration, the degree of support may be adjusted to accommodate varying anatomical conditions and degrees of urinary incontinence. The control mechanism 4 used to adjust the degree of support may be one of the mechanical variants as shown in FIGS. 11 and 12, or the electro-mechanical variant shown in FIG. 13. The ends 42 of the elevating tape 43 may be fixed to the pubic bone or endopelvic facsia by sutures or screws. As load applied to the traction sutures 41 by the control mechanism 4, the elevating tape 43 may elevate the urethra, thereby compressing it from the underside and increasing the intra-urethral pressure to prevent leakage.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled,

We claim:

1. An implantable apparatus for occluding a fluid conveying body vessel comprising:

an outer sheath having an internal space that is configured to retain a liquid, the outer sheath being water tight and having a first end and a second end, at least a portion of the outer sheath configured to at least partially encircle the fluid conveying body vessel;

an inner occlusive tape disposed through the inner space, the inner occlusive tape having a first end and a second end, wherein the first end of the inner occlusive tape is fixed to the first end of the outer sheath, the second end of the inner occlusive tape is movable relative to the outer sheath, and the inner occlusive tape having a rectangular cross-section with a varied width from the first end to the second end of the inner occlusive tape; and a control mechanism connected to the second end of the inner occlusive tape, the control mechanism having an activated state and a deactivated state, wherein in the activated state the control mechanism applies a tension to the inner occlusive tape so that the inner occlusive tape applies a pressure to the portion of the outer sheath encircling the fluid conveying body vessel, and when the inner occlusive tape is adjusted to encircle the fluid conveying body vessel, the varied width of the inner occlusive tape is configured to increase or decrease the pressure on the fluid conveying body vessel, and in the deactivated state the control mechanism releases the tension from the inner occlusive tape so that the inner occlusive tape releases the pressure from the portion of the outer sheath encircling the fluid conveying body vessel.

2. The implantable apparatus for occluding a fluid conveying body vessel of claim 1, wherein the varied width of the inner occlusive tape is tapered from the first end to the second end of the inner occlusive tape, the varied width of the inner occlusive tape has a first width at the first end of the inner occlusive tape and a second width at the second end of the inner occlusive tape, and the second width is greater than the first width.

3. The implantable apparatus for occluding a fluid conveying body vessel of claim 1 further comprising
a locking clip attached to the second end of the outer sheath; and
a plurality of locking detents on an outer surface of the outer sheath,
wherein engaging a different detent of the plurality of the locking detents to the clip adjusts a circumference of the portion of the outer sheath configured to at least partially encircle the fluid conveying body vessel.

4. The implantable apparatus for occluding a fluid conveying body vessel of claim 1 further comprising a bleed valve connected to the first end of the outer sheath, wherein the bleed valve has an open position and a closed position, the open position is configured to allow air out of the inner space of the outer sheath and the close position is water tight.

5. The implantable apparatus for occluding a fluid conveying body vessel of claim 1, wherein the inner space of the outer sheath is filled with a liquid.

6. The implantable apparatus for occluding a fluid conveying body vessel of claim 1, wherein when the inner occlusive tape is adjusted to encircle the fluid conveying body vessel, the varied width of the inner occlusive tape is configured to increase or decrease the pressure on the fluid conveying body vessel so that a urethral pressure in the fluid conveying body vessel is in a range of 50-80 cm $H_2O$.

7. The implantable apparatus for occluding a fluid conveying body vessel of claim 1, wherein the varied width is between 3 mm and 10 mm.

8. An occlusive member for an occlusive device comprising:
an outer sheath having an inner space that is configured to retain liquid, the outer sheath being water tight and having a first end and a second end, at least a portion of the outer sheath configured to at least partially encircle a fluid conveying body vessel; and an inner occlusive tape disposed through the inner space of the outer sheath, the inner occlusive tape having a first end and a second end, wherein the first end of the inner occlusive tape is fixed to the first end of the outer sheath, the second end of the inner occlusive tape is movable relative to the outer sheath and configured to receive a tension and the inner occlusive tape having a rectangular cross-section from the first end to the second end;

wherein when the second end of the inner occlusive tape is under tension the inner occlusive tape applies a pressure to the portion of the outer sheath encircling the fluid conveying body vessel;

and the inner occlusive tape has a varied width from the first end to the second end of the inner occlusive tape, and when the inner occlusive tape is adjusted to encircle the fluid conveying body vessel, the varied width of the inner occlusive tape is configured to increase or decrease the pressure on the fluid conveying body vessel.

9. The occlusive member for an occlusive device of claim 8, wherein the varied width of the inner occlusive tape is tapered from the first end to the second end of the inner occlusive tape, the varied width of the inner occlusive tape has a first width at the first end of the inner occlusive tape and a second width at the second end of the inner occlusive tape, and the second width is greater than the first width.

10. The occlusive member for an occlusive device of claim 8 further comprising a locking clip attached to the second end of the outer sheath; and a plurality of locking detents on an outer surface of the outer sheath, wherein engaging a different detent of the plurality of the locking detents to the clip adjusts a circumference of the portion of the outer sheath configured to at least partially encircle the fluid conveying body vessel.

11. The occlusive member for an occlusive device of claim 8 further comprising a bleed valve connected to the first end of the outer sheath, wherein the bleed valve has an open position and a closed position, the open position is configured to allow air out of the inner space of the outer sheath and in the closed position the bleed valve is water tight.

12. The occlusive member for an occlusive device of claim 8, wherein the inner space of the outer sheath is filled with a liquid.

13. A method of applying an occlusive pressure to a tubular body passage comprising:
implanting an occlusive device inside a body, the occlusive device comprising an occlusive member that has an outer sheath and an inner occlusive tape, the outer sheath being water tight and having an inner space, the inner occlusive tape disposed through the inner space of the outer sheath, the inner occlusive tape having a first end and a second end, wherein the first end of the inner occlusive tape is fixed to the first end of the outer sheath, and the second end of the inner occlusive tape is movable relative to the outer sheath and configured to receive a tension;
wrapping at least partially a tubular body passage with at least a portion of the outer sheath;
filling a liquid in the inner space of the outer sheath;
adjusting the inner occlusive tape to encircle the tubular body passage; and applying a tensioning force to the second end of the inner occlusive tape so that the inner occlusive tape applies a pressure to the portion of the outer sheath wrapping the tubular body passage;

wherein the inner occlusive tape has a rectangular cross-section with a varied width from the first end to the second end of the inner occlusive tape, and when the inner occlusive tape is adjusted to encircle the tubular body passage, the varied width of the inner occlusive tape is configured to increase or decrease the pressure on the tubular body passage.

14. The method of applying an occlusive pressure to a tubular body passage of claim 13 further comprising locking the first end of the outer sheath with a locking clip so that the at least portion of the outer sheath encircling at least partially the tubular body passage does not change.

15. The method of applying an occlusive pressure to a tubular body passage of claim 13, wherein the varied width of the inner occlusive tape is tapered from the first end to the second end of the inner occlusive tape, and the varied width decreases from the second to the first end.

16. The method of claim 15, further comprising:

positioning a portion of the inner occlusive tape to encircle the tubular body passage, so that when applying the tensioning force to the second end of the inner occlusive tape, the tapered width of the portion of the inner occlusive tape encircling the tubular body passage is configured to provide a pressure to occlude the tubular body passage.

17. The method of claim 16, further comprising:

moving the portion of the inner occlusive tape to encircle the tubular body toward the first end to increase the pressure applied by the inner occlusive tape to the tubular body passage when applying the tensioning force to the second end of the inner occlusive tape; or moving the portion of the inner occlusive tape to encircle the tubular body toward the second end to decrease the pressure applied by the inner occlusive tape to the tubular body passage when applying the tensioning force to the second end of the inner occlusive tape.

* * * * *